United States Patent [19]

Aratani et al.

[11] 4,197,408
[45] Apr. 8, 1980

[54] ASYMMETRIC SYNTHESIS OF ALKYL CHRYSANTHEMATE

[75] Inventors: Tadatoshi Aratani; Yukio Yoneyoshi, both of Takatsuki; Fumio Fujita, Osaka; Tsuneyuki Nagase, Takatsuki, all of Japan

[73] Assignee: Sumitomo Chemical Company, Limited, Osaka, Japan

[21] Appl. No.: 847,471

[22] Filed: Oct. 31, 1977

Related U.S. Application Data

[63] Continuation of Ser. No. 710,855, Aug. 2, 1976, abandoned.

[30] Foreign Application Priority Data

Aug. 1, 1975 [JP] Japan .................................. 50/94349

[51] Int. Cl.$^2$ .............................................. C07C 51/00
[52] U.S. Cl. .................................................... 560/124
[58] Field of Search ......................................... 560/124

[56] References Cited

U.S. PATENT DOCUMENTS

| | | | |
|---|---|---|---|
| 3,868,401 | 2/1975 | Aratani et al. | 560/124 |
| 4,029,690 | 6/1977 | Aratani | 560/124 |

FOREIGN PATENT DOCUMENTS

| | | | |
|---|---|---|---|
| 2407094 | 9/1974 | Fed. Rep. of Germany | 560/124 |
| 40-6457 | 3/1965 | Japan | 560/124 |
| 49-14448 | 2/1974 | Japan | 560/124 |
| 49-66660 | 6/1974 | Japan | 560/124 |

OTHER PUBLICATIONS

Aratani, Tetrahedron Letters, 21, pp. 1707-1710.

*Primary Examiner*—Bernard Helfin
*Assistant Examiner*—Michael Shippen
*Attorney, Agent, or Firm*—Wenderoth, Lind & Ponack

[57] ABSTRACT

A process for the production of an optically active chrysanthemate which comprises reacting 2,5-dimethyl-2,4-hexadiene with a diazoacetate of the formula:

N$_2$CHCOOR wherein R is selected from the group consisting of (a) cycloalkyl group with or without substituent(s) whose total carbon atom number is 5–20, (b) tertiary aralkyl group whose carbon atom number is 9 to 20, and (c) tertiary alkyl group with or without alkoxy substituent(s) whose total carbon atom number is 4–20, in the presence of a copper complex coordinated with a chiral Schiff base of the formula:

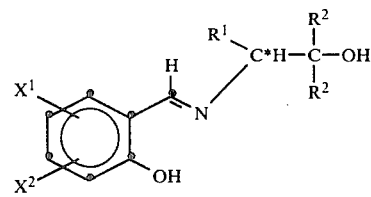

wherein C* is an asymmetric carbon atom, R$^1$ is selected from the group consisting of (a) alkyl groups whose carbon atom number is 1–10 and (b) aralkyl groups with or without alkoxy substituent(s), whose total carbon atom number is 7–20, R$^2$ is selected from aryl groups with alkoxy substituent(s), whose total carbon atom number is 7–30, and each of X$^1$ and X$^2$ is selected from the group consisting of (a) hydrogen atom, (b) alkyl groups having 1–10 carbon atoms, (c) phenyl group, (d) alkoxy groups having 1–10 carbon atoms, (e) halogen atoms and (f) nitro group, or (g) X$^1$ and X$^2$ together form a benzo group.

6 Claims, No Drawings

ASYMMETRIC SYNTHESIS OF ALKYL CHRYSANTHEMATE

This is a continuation of application Ser. No. 710,855, filed Aug. 2, 1976, now abandoned.

The present invention relates to a process for producing an optically active chrysanthemate wherein 2,5-dimethyl-2,4-hexadiene is reacted with a diazoacetate in the presence of a copper complex coordinated with a novel kind of Schiff base.

Chrysanthemic acid is an important material for the production of synthetic pyrethroids which are effective as insecticides. There are four stereoisomers of chrysanthemic acid: two kinds of geometric isomers, i.e. cis and trans, each having d and l optical isomers. The pyrethroids derived from d-trans and d-cis chrysanthemic acids are known to be particularly effective in insecticidal activity. In this connection, naturally occurring chrysanthemic acid is known to have d-trans structure.

Two industrial methods are possible to prepare optically active chrysanthemic acid. In one method, the racemic mixture is synthesized first, and is subsequently subjected to optical resolution. The other method is direct asymmetric synthesis of the desired optical isomer.

One of the synthetic processes for preparing chrysanthemic acid is to react an alkyl diazoacetate with 2,5-dimethyl-2,4-hexadiene in the presence of a copper catalyst (see British Pat. No. 740,014) and then to hydrolyze the resulting alkyl chrysanthemate.

This invention is concerned with the asymmetric synthesis of chrysanthemates. In our Belgian Pat. No. 787,473, there is described and claimed a process for producing an optically active chrysanthemate by reacting a diazoacetate with 2,5-dimethyl-2,4-hexadiene in the presence of a copper catalyst coordinated with a chiral ligand according to the following equation:

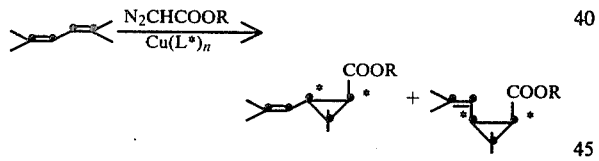

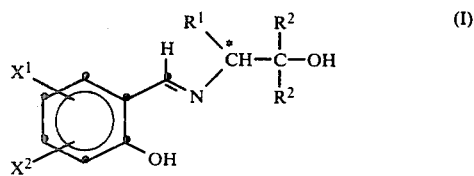

wherein L* is a chiral ligand.

We have found, in our Belgian Pat. No. 810,959, that it is advantageous to catalyse the asymmetric synthesis of chrysanthemates with a copper complex coordinated with chiral Schiff base having the following formula:

(I)

wherein C* is an asymmetric carbon atom, R¹ is selected from the group consisting of (a) alkyl groups whose carbon atom number is 1-10, and (b) aralkyl groups with or without alkoxy substituent(s), whose total carbon atom number is 7-20, R² is selected from aryl groups with alkoxy substituent(s), whose total carbon atom number is 7-30, and each of X¹ and X² is selected from the group consisting of (a) hydrogen atom, (b) alkyl groups having 1-10 carbon atoms, (c) phenyl group, (d) alkoxy groups having 1-10 carbon atoms, (e) halogen atoms and (f) nitro group, or (g) X¹ and X² together form a benzo group.

In the following a further explanation will be given the novel kind of chiral copper complexes used as catalysts in our Belgian Pat. No. 810,959.

When the Schiff base of the formula (I) forms a metal complex with divalent copper ion, three kinds of chelates are possible. (For the chemistry of metal complexes of Schiff bases, see R. H. Holm, G. W. Everett, Jr., and A Chakravorty "Progress in Inorganic Chemistry" 7, 83–214, (1966), Interscience Publishers, New York)

One has the following dimeric structure (II) wherein the Schiff base behaves as tridentate ligand:

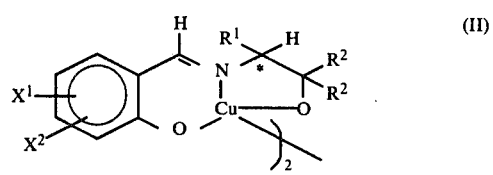

wherein R¹, R², X¹ and X² are as defined above. The other two have the following monomeric structure (III) or (IV) wherein the Schiff base behaves as bidentate or tridentate ligand, respectively,

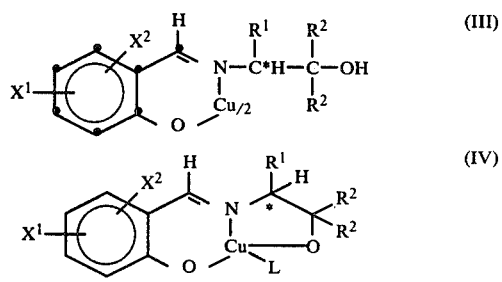

wherein R¹, R², X¹ and X² are as defined above, and L is a neutral monodentate ligand. (For the copper complexes of N-salicylidene-2-aminoethanol, see R. P. Houghton and D. J. Pointer, J. Chem. Soc. 4214 (1965))

We further made a study on the diazoacetate used as the substrate in this asymmetric synthesis. As a result, we found that the diazoacetate represented by the general formula:

$$N_2CHCOOR \qquad (V)$$

wherein R is selected from the group consisting of (a) cycloalkyl group with or without alkyl substituent(s) whose total carbon atom number is 5 to 20, (b) tertiary aralkyl group whose carbon atom number is 9 to 20, and (c) tertiary alkyl group with or without alkoxy substituent(s) whose total carbon atom number is 4–20, is particularly effective for obtaining the resulting chrysanthemate with an excellent optical purity as well as high trans isomer content. This fact is quite unexpected from reaction results using primary diazoacetate of lower aliphatic alcohol having 1-8 carbon atom(s) such as ethyl ester.

The present invention has been accomplished on the basis of this new knowledge. That is to say, the present invention is a process for producing an optically active chrysanthemate characterized by the reaction of a diazoacetate represented by the general formula (V) with 2,5-dimethyl-2,4-hexadiene in the presence of, as catalyst a chiral copper complex derived from the optically active Schiff base, for example those having monomeric structure as shown by the general formula (III) or (IV), or those having dimeric structure as shown by the general formula (II).

The substituent group R of the diazoacetate represented by the general formula (V) is previously mentioned, but concretely the following is exemplified:

(a) Among the cycloalkyl groups, there may be recited cyclopentyl, 2-methylcyclopentyl, cyclohexyl, 2-methylcyclohexyl, 2,2-, 2,5- or 2,6-dimethylcyclohexyl, 2,2,6-trimethylcyclohexyl, cyclooctyl, cyclododecyl, etc. Cycloalkyl groups of naturally or non-naturally occurring alicyclic alcohols are also effective. For example, menthyl, isomenthyl, neomenthyl, neoisomenthyl, carbomenthyl, bornyl, isobornyl, 2-norbornyl, 1- and 2-adamantyl, etc. may be mentioned.

(b) Among tertiary aralkyl groups, there may be recited α,α-dimethylbenzyl, triphenylmethyl, α,α-diphenylethyl, 2-phenyl-2-butyl, etc.

(c) Among tertiary alkyl groups, there may be recited t-butyl, t-amyl, 2,3-dimethyl-2-butyl, 2,3,4-trimethyl-3-pentyl, α,α-dimethyl-β-menthoxyethyl, etc.

The diazoacetates of the general formula (V) can have either achiral or chiral structure. In the latter case, either form of enantiomers or racemic modification can be used for the present reaction. When chrysanthemate formed by the present reaction shows some insecticidal activity, it may be used as an insecticide as itself.

Although there is no limitation on the processes for synthesizing the diazoacetate of the formula (V), the following processes may be exemplified:

(i) A method of diazotizing the corresponding ester of glycine with nitrous acid or a nitrous acid ester. Refer for example to Organic Syntheses, Coll. Vol. 4, 424 and N. Takamura, T. Mizoguchi, K. Koga and S. Yamada, Tetrahedron 31, 227 (1975). The ester of glycine can be synthesized by the reaction of glycine with the corresponding alcohol or the corresponding olefin.

(ii) A method of Regitz: p-toluenesulfonylazide is reacted with the corresponding acetoacetate, and the resulting 2-diazoacetoacetate is deacetylated with a base to give diazoacetate. Refer, for example, to Organic Syntheses, Coll. Vol. 5, p. 179.

(iii) A method of House: Acid chloride of the p-toluenesulfonylhydrazone of glyoxylic acid chloride is reacted with the corresponding alcohol in the presence of a base. Refer, for example, to Organic Syntheses, Coll. Vol. 5, p. 258.

The chiral Schiff base of the formula (I) is synthesized by the reaction of a chiral amino alcohol having the formula (VI) with a salicylaldehyde derivative having the formula (VII):

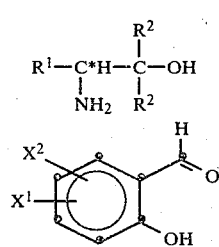

wherein $R^1$, $R^2$, $X^1$ and $X^2$ are as defined above.

Specific examples of the substituents $R^1$ and $R^2$ in the amino alcohol (VI) are methyl, ethyl, propyl, isopropyl, butyl, isobutyl, 2-butyl, t-butyl, hexyl, octyl, cyclohexylmethyl, benzyl, benzhydryl and 2,2-diphenylethyl. Among these examples, preferred substituents are methyl, isopropyl, isobutyl, cyclohexylmethyl, benzyl, and a benzyl group having a substituent at the 4-position of the aromatic neucleus, of which the substituent is, for example, methoxy, ethoxy, propoxy, isopropoxy, butoxy, or hexyloxy, etc. As $R^2$ in the amino alcohol, a phenyl group having a substituent at the 2-position or having substituents at the 2,5-positions is preferred. Specific examples of 2-substituted phenyl groups are 2-methoxyphenyl, 2-ethoxyphenyl, 2-propoxyphenyl, 2-isopropoxyphenyl, 2-butoxyphenyl, 2-t-butoxyphenyl, 2-hexyloxyphenyl, 2-octyloxyphenyl, etc. Specific examples of 2,5-substituted phenyl groups are 2-methoxy-5-methylphenyl, 2-butoxy-5-methylphenyl, 5-methyl-2-octyloxyphenyl, 2-benzyloxy-5-methylphenyl, 5-t-butyl-2-methoxyphenyl, 2-butoxy-5-t-butylphenyl, 5-t-butyl-2-octyloxyphenyl, 4-methoxybiphenyl-3-yl, 4-butoxybiphenyl-3-yl, 4-octyloxybiphenyl-3-yl, 2,5-dimethoxyphenyl, 2,5-dibutoxyphenyl, 2,5-dioctyloxyphenyl, etc.

The optically active amino alcohols of the formula (VI) to be used in this invention may be prepared in any of the following two ways, i.e. one is to resolve a racemic mixture of the corresponding amino alcohol with an appropriate resolving agent, and the other is to prepare the amino alcohol from the reaction of optically active precursor. Thus, for example, reaction of an optically active amino ester of the following formula (VIII) with a Grignard reagent of the following formula (IX) gives the optically active amino alcohol (VI) with retention of configuration.

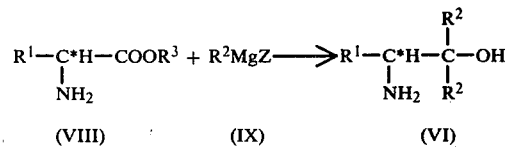

wherein $R^1$ is alkyl or aralkyl, $R^2$ is aryl, $R^3$ is alkyl of 1–10 carbon atoms or benzyl and Z is chlorine, bromine or iodine. As for the addition reaction of phenyl magnesium bromide to (L)-alanine ethyl ester, see for example A. McKenzie, R. Roger, G. O. Willis, J. Chem. Soc., 779 (1926) and B. M. Benjamin, H. J. Schaefer, C. J. Collins, J. Am. Chem. Soc., 79 6160 (1957).

Specific examples of the salicylaldehyde derivatives (VII) are salicylaldehyde, 3-ethoxysalicylaldehyde, o-vanilline, 3,5-dibromosalicylaldehyde, 5-chlorosalicylaldehyde, 3-nitrosalicylaldehyde, 3-isopropyl-6-methylsalicylaldehyde, 2-hydroxy-naphthaldehyde, 1-hydroxy-2-naphthaldehyde and the like.

Among the chiral copper complexes employed as catalysts in the present invention, specific examples of the copper complexes (II), (III) and (IV) are those that are derived from the following chiral Schiff bases:

(a) N-salicylidene-2-amino-1,1-di(2-methoxyphenyl)-3-phenyl-1-propanol, (b) N-salicylidene-2-amino-1,1-di(2-isopropoxyphenyl)-3-phenyl-1-propanol, (c) N-salicylidene-2-amino-1,1-di(5-t-butyl-2-isopropoxyphenyl)-3-phenyl-1-propanol, (d) N-salicylidene-2-amino-1,1-di(2-butoxy-5-t-butylphenyl)-3-phenyl-1-propanol,
(e) N-salicylidene-2-amino-1,1-di(5-t-butyl-2-heptyloxyphenyl)-3-phenyl-1-propanol,
(f) N-salicylidene-2-amino-1,1-di(5-t-butyl-2-isopropoxyphenyl)-1-propanol,
(g) N-salicylidene-2-amino-1,1-di(2-butoxy-5-t-butylphenyl)-1-propanol,
(h) N-salicylidene-2-amino-1,1-di(5-t-butyl-2-octyloxyphenyl)-1-propanol,
(i) N-(3-methoxysalicylidene)-2-amino-1,1-di(5-t-butyl-2-octyloxyphenyl)-1-propanol,
(j) N-(3,5-dibromosalicylidene)-2-amino-1,1-di(2-isopropoxyphenyl)-3-phenyl-1-propanol,
(k) N-(3-ethoxysalicylidene)-2-amino-1,1-di(2-isopropoxyphenyl)-3-phenyl-1-propanol,
(l) N-(2-hydroxy-1-naphthylmethylene)-2-amino-1,1-di(2-isopropoxyphenyl)-3-phenyl-1-propanol,
(m) N-salicylidene-2-amino-1,1-di(4-butoxydiphenyl-3-yl)-3-phenyl-1-propanol,
(n) N-salicylidene-2-amino-1,1-di(2,5-dibutoxyphenyl)-3-phenyl-1-propanol,
(o) N-salicylidene-2-amino-1,1-di(2-butoxyphenyl)-3-methyl-1-butanol, or
(p) N-salicylidene-2-amino-1,1-di(2-butoxy-5-t-butylphenyl)-4-methyl-1-pentanol.

As copper complexes of the optically active Schiff base of the formula (I), copper complexes of the previously mentioned general formulae (II), (III) and (IV) are effective, but the complex having dimeric structure of the formula (II) is used particularly advantageously. The complex of the general formula (II) is synthesized by the reaction of the Schiff base of the general formula (I) with a cupric salt such as cupric acetate.

The complex having monomeric structure of the formula (IV) is synthesized by the reaction of the dimeric complex of the general formula (II) with a neutral monodentate ligand, for example pyridine, picoline, lutidine, etc. The complex having monomeric structure of the formula (III) is synthesized by reacting a copper complex of the salicylaldehyde derivative of the formula (VII) with the amino alcohol of the formula (VI).

In the actual practice of the present invention, the reaction can be carried out regardless of whether the chiral copper catalyst is soluble or insoluble in the reaction system.

The catalyst may be recovered and purified by an appropriate method for repeated use.

Preferably, the molar ratio of the copper complex to diazoacetate (V) is in a range of 0.001–0.1.

Although the reaction temperature is not particularly limited, usually a temperature between −50° C. and 150° C. is suitable. In particular cases of carrying out the reaction at a temperature below the melting point of 2,5-dimethyl-2,4-hexadiene (15° C.), a suitable solvent may be desirably added to the reaction system. Aromatic hydrocarbons such as benzene, toluene and xylene are suitable as the solvent in such cases.

The present invention is explained in further detail by the examples set forth below. They are not, however, to be taken as being limitative thereof.

In general, an unequivocal correlation exists between the absolute configuration of the substance which induces asymmetry and the absolute configuration of the substance to which asymmetry is induced. Therefore, in this invention, too, it is needless to say that when the copper complex of enantiomeric structure opposite to the one described in the following examples is used as the catalyst, the resulting chrysanthemate and the corresponding chrysanthemic acid will also have the opposite enantiomeric structure.

EXAMPLE 1

An amount of 0.3 g. (0.2 m mol) of the dimeric copper complex of (R)-N-salicylidene-2-amino-1,1-di(5-t-butyl-2-octyloxy)-propanol (corresponding to the formula (II) wherein $R^1$=methyl, $R^2$=5-t-butyl-2-octyloxyphenyl, and $X^1$=$X^2$=hydrogen) was dissolved in 17.6 g. (160 m mols) of 2,5-dimethyl-2,4-hexadiene. To this solution, was added dropwise a mixture of 4.4 g. (40 m mols) of the above mentioned diene and 4.5 g. (20 m mols) of l-mentyl diazoacetate with stirring over a period of 7 hours. At the beginning of the addition, the solution of catalyst was once heated to 75° C. to initiate the decomposition of diazoacetate and thereafter the mixture was maintained at 40° C. At the end of the addition, a nearly quantitative amount of nitrogen gas was evolved.

The reaction mixture was distilled to recover the unreacted excess diene (boiling point 45° C./20 mm Hg) under reduced pressure, and 4.7 g. of l-menthyl chrysanthemate was obtained as an oil having a boiling point of 123° C./0.2 mm Hg. The yield was 76% based on the diazo compound.

The l-menthyl ester was analyzed on a gas chromatograph equipped with a glass capillary column (liquid phase QF-1) to determine the composition of optical isomers of the chrysanthemate.

d-trans form 89.9%; l-trans form 2.7%; total of d-cis and l-cis forms (separation was impossible) 7.4%.

It is calculated that the percentage of the trans isomer in the ester is 93%, and the optical purity of the trans isomers is 92%.

A mixture of 4.2 g. of l-menthyl ester, 1.8 g. of potassium hydroxide, 1.5 ml. of water and 11 ml. of ethanol was heated at 100° C. with stirring for 7.5 hours. After distillation of ethanol from the reaction mixture, the residue was diluted with water and was extracted with ether. The alkaline aqueous solution was acidified with dilute sulfuric acid, and was extracted with toluene. After the organic layer was washed with water and dried, toluene was distilled off under reduced pressure to give chrysanthemic acid (2.4 g., yield 90%).

Chrysanthemic acid was reacted with d-2-octanol and the resulting diasteromers were analyzed by gas chromatography to determine the composition of optical isomers of chrysanthemic acid.

d-trans form 90.4%; l-trans form 4.7%; d-cis form 3.6%; l-cis form 1.3%.

It is calculated that the optical purity of the trans isomers is 90% and that of the cis isomer is 50%.

For the analysis of chrysanthemic acid, refer to A. Murano, Agr. Biol. Chem., 36, 2203 (1972).

EXAMPLES 2–6

Similar experiments as in Example 1 were performed, using dimeric chiral copper complexes shown in Table 1 and l-menthyl diazoacetate. The results are summarized in Table 1. The content of the trans isomer of l-menthyl chrysanthemate was determined by gas chromatography. The optical purity of chrysanthemic acid obtained after hydrolysis was determined by gas chromatographic analysis of the corresponding (S)-l-menthylheptyl ester.

It should be noted that when a catalyst of (R) configuration is used, dextrorotatory-chrysanthemic acid is the favoured product, and when a catalyst of (S) configuration is used, laevorotatory-chrysanthemic acid is the favoured one.

REFERENCE EXAMPLE 1

In place of chiral copper complex, copper powder was used as catalyst in the reaction between 1-menthyl diazoacetate and 2,5-dimethyl-2,4-hexadiene. The results are shown in Table 1.

Table 1

| | Synthesis of 1-menthyl chrysanthemate | | | | | | |
|---|---|---|---|---|---|---|---|
| | Chiral copper complex (II) | | | Reaction temp. (°C.) | Chrysanthemate | | Optical purity of the acid, % |
| Example No. | Configuration | $R^1$ | $R^2$ | | Yield (%) | trans (%) | trans / cis |
| 2 | (S) | methyl | 5-t-butyl-2-octyloxyphenyl | 40 | 64 | 72 | 90 / 59 |
| 3 | (S) | methyl | 5-t-butyl-2-isopropoxyphenyl | 40 | 69 | 70 | 88 / 60 |
| 4 | (R) | methyl | 5-t-butyl-2-butoxyphenyl | 60 | 67 | 89 | 87 / 25 |
| 5 | (R) | benzyl | 5-t-butyl-2-heptyloxyphenyl | 40 | 42 | 91 | 86 / 22 |
| 6 | (S) | benzyl | 5-t-butyl-2-heptyloxyphenyl | 40 | 36 | 75 | 86 / 5 |
| Reference Example 1 | Copper powder | | | 123 | 69 | 76 | 0.7 / 0 |

EXAMPLES 7–16

Similar experiments as in Example 1 were performed, using diazoacetates of Table 2 and a chiral copper complex (the formula (II) wherein the configuration is (R), $R^1$ = methyl, $R^2$ = 5-t-butyl-2-octyloxyphenyl). The results are summarized in Table 2. The content of trans isomer in the alkyl chrysanthemates was determined by gas chromatography. The optical purity of chrysanthemic acid obtained after hydrolysis of the esters was determined by gas chromatographic analysis of corresponding (S)-1-menthyl-1-heptyl ester.

The diazoacetates used in the examples were synthesized either by the following (A) method or (B) method.

In (A) method, a corresponding glycine ester is diazotized with isoamyl nitrite. The process is shown as follows:

ROH→H$_2$NCH$_2$COOR→N$_2$CHCOOR

As a typical example, the preparation of 1-menthyl diazoacetate is shown in Example 17.

In (B) method, the reaction proceeds as follows:

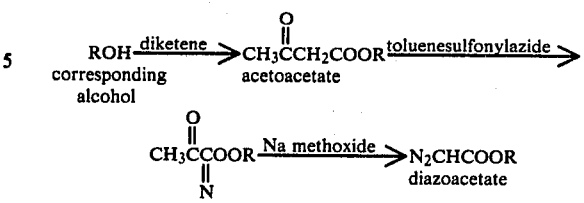

As a typical example, the preparation of 2,3,4-trimethyl-3-pentyl diazoacetate is shown in Example 18.

Table 2

| | Synthesis of chrysanthemates | | | | | | |
|---|---|---|---|---|---|---|---|
| | Diazoacetates | | Reaction temp. (°C.) | Chrysanthemates | | Optical purity of chrysanthemates, % | |
| Example No. | R | Method of synthesis | | Yield (%) | trans (%) | trans | cis |
| 7 | dl-menthyl | A | 40 | 67 | 81 | 90 | 75 |
| 8 | d-neomenthyl | A | 65 | 77 | 89 | 87 | — |
| 9 | dl-bornyl | A | 40 | 74 | 68 | 70 | 74 |
| 10 | 1-adamantyl | A | 23 | 82 | 68 | 85 | 46 |
| 11 | cyclohexyl | B | 40 | 71 | 58 | 70 | 58 |
| 12 | α,α-dimethyl-β-(1-menthoxy)ethyl | A | 40 | 80 | 79 | 86 | 45 |
| 13 | t-butyl | B | 60 | 74 | 75 | 75 | 46 |
| 14 | 2,3,dimethyl-2-butyl | B | 40 | 71 | 78 | 85 | 43 |
| 15 | 2,3,4-trimethyl-3-pentyl | B | 40 | 64 | 92 | 88 | — |
| 16 | α,α-dimethyl-benzyl | B | 40 | 60 | 56 | 71 | — |
| Reference Example 2 | ethyl | — | 40 | 54 | 51 | 68 | 62 |

REFERENCE EXAMPLE 2

Using the same copper catalyst as in Examples 6–16, the reaction between ethyl diazoacetate and 2,5-dimethyl-2,4-hexadiene was carried out. The results are shown in Table 2.

EXAMPLE 17

A mixture of 1-menthyl glycine (19.7 g.; 0.092 mol), isoamyl nitrite (12.0 g.; 0.10 mol) and acetic acid (1.6 g.; 0.027 mol) in chloroform (400 ml) was heated with stirring for 25 minutes under reflux. The reaction mixture was washed with 1-N sulfuric acid followed by a saturated aqueous solution of sodium bicarbonate and then water. After the organic phase was dried, the residue (21 g.) obtained by condensation was purified by column chromatography (silica gel 160 g., methylene chloride) to give l-menthyl diazoacetate (15.0 g., 73%).

Yellow crystal, $[\alpha]_D - 86.8°$ (chloroform, c 1.0),
IR (film) $\gamma 2125$ cm$^{-1}$
NMR (chloroform, TMS) $\delta$ 5.29 ppm.

For l-menthyl glycine, refer to K. Harada, T. Hayakawa, Bull. Chem. Soc. Japan, 37, 191 (1964).

EXAMPLE 18

To a mixture of 2,3,4-trimethyl-3-pentanol (24.3 g.; 0.18 mol) and triethylamine (0.1 g.) was added diketene (15.7 g.; 0.186 mol) dropwise at 70° C. After the reaction mixture was stirred at 110° C. for 1.5 hours, it was distilled under reduced pressure to give the corresponding acetoacetate (boiling point 84° C./0.6 mm; 35.3 g.; 88%).

To a mixture of the above mentioned ester (35.3 g., 0.164 mol), triethylamine (17 g., 0.168 mol) and acetonitrile (200 ml) was added p-toluenesulfonylazide (38 g., 0.164 mol) dropwise at room temperature. After the reaction mixture was stirred for 1.5 hours, it was concentrated under reduced pressure. The residue was extracted with ether (200 ml) and the organic phase was washed twice with an aqueous solution of potassium hydroxide (12.6 g.). The organic phase was dried and concentrated to give the corresponding α-diazoacetoacetate (40 g.).

To a solution of above ester (40 g.) in methanol (65 ml) was added a sodium methoxide solution prepared from sodium (4.2 g.) and methanol (65 ml) at 0° C. After the reaction mixture was further stirred for one hour at 0° C., ice water (300 ml) was poured thereto, sodium chloride was added and the mixture was extracted with ether (400 ml in total). After the organic phase was washed with water and dried, it was concentrated and distilled to give 2,3,4-trimethyl-3-pentyl diazoacetate (b.p. 59° C./0.2 mm; 20 g.; 64%).

Yellow oil, IR (film) $\gamma$ 2125 cm$^{-1}$
NMR (chloroform, TMS) $\delta$ 5.40 ppm.

What we claim is:

1. A process for producing an optically active chrysanthemate which comprises reacting 2,5-dimethyl-2,4-hexadiene with a diazoacetate of the formula

N$_2$CHCOOR wherein R is selected from the group consisting of menthyl, neomenthyl, 1-adamantyl, α,α-dimethyl-β(menthoxy)-ethyl, 2,3-dimethyl-2-butyl and 2,3,4-trimethyl-3-pentyl, in the presence of a copper complex of the formula

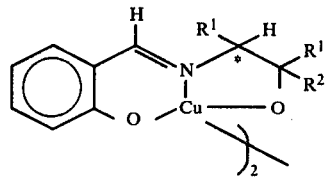

wherein * designates an asymmetric carbon atom, R$^1$ is selected from the group consisting of benzyl and methyl, and R$^2$ is selected from the group consisting of 5-t-butyl-2-isopropoxyphenyl, 5-t-butyl-2-heptyloxyphenyl, 2-butoxy-5-t-butylphenyl and 5-t-butyl-2-octyloxyphenyl.

2. The process according to claim 1, wherein the copper complex is a copper complex of a (R)-enantiomer of a chiral Schiff base selected from the group consisting of N-salicylidene-2-amino-1,1-di(5-t-butyl-2-heptyloxyphenyl)-3-phenyl-1-propanol, N-salicylidene-2-amino-1,1-di(5-t-butyl-2-isopropoxyphenyl)-1-propanol, N-salicylidene-2-amino-1,1-di(2-butoxy-5-t-butylphenyl)-1-propanol and N-salicylidene-2-amino-1,1-di(5-t-butyl-2-octyloxyphenyl)-1-propanol.

3. The process according to claim 1, wherein R is selected from the group consisting of menthyl, neomenthyl and 1-adamantyl.

4. The process according to claim 1, wherein the reaction is conducted in the absence of a solvent.

5. The process according to claim 1, wherein the reaction temperature is in a range of from −50° C. to 150° C.

6. The process according to claim 1, wherein the molar ratio of the copper complex to the diazoacetate is in a range of 0.001 to 0.1.

* * * * *